US012433992B2

(12) United States Patent
Park

(10) Patent No.: US 12,433,992 B2
(45) Date of Patent: Oct. 7, 2025

(54) LIQUID INFUSION DEVICE EQUIPPED WITH A MAGNETIC RETURN-TO-ORIGIN AND FIXATION MEANS

(71) Applicant: CureStream Co., Ltd, Daegu (KR)

(72) Inventor: Dae Jong Park, Seoul (KR)

(73) Assignee: CURESTREAM CO., LTD, Daegu (KR)

( * ) Notice: Subject to any disclaimer, the term of this patent is extended or adjusted under 35 U.S.C. 154(b) by 0 days.

(21) Appl. No.: 18/909,497

(22) Filed: Oct. 8, 2024

(65) Prior Publication Data

US 2025/0121129 A1 Apr. 17, 2025

(30) Foreign Application Priority Data

Oct. 12, 2023 (KR) ........................ 10-2023-0135851

(51) Int. Cl.
*A61M 5/142* (2006.01)
*F04B 17/04* (2006.01)

(52) U.S. Cl.
CPC ......... *A61M 5/14216* (2013.01); *F04B 17/04* (2013.01)

(58) Field of Classification Search
CPC ............................ A61M 5/14216; F04B 17/04
See application file for complete search history.

(56) References Cited

U.S. PATENT DOCUMENTS

| | | | | | |
|---|---|---|---|---|---|
| 4,218,669 | A * | 8/1980 | Hitchcock | H01F 7/1607 | 335/258 |
| 4,425,889 | A * | 1/1984 | Hachitani | F02D 31/007 | 123/357 |
| 4,463,332 | A * | 7/1984 | Everett | H01F 7/13 | 335/274 |
| 5,362,209 | A * | 11/1994 | Day | F02D 1/08 | 417/293 |
| 2016/0166761 | A1* | 6/2016 | Piehl | A61B 17/3498 | 604/207 |
| 2017/0281875 | A1* | 10/2017 | Piehl | A61M 5/1782 | |

FOREIGN PATENT DOCUMENTS

| | | | |
|---|---|---|---|
| JP | 2018-175180 | A | 11/2018 |
| KR | 10-2538410 | B1 | 6/2023 |

* cited by examiner

*Primary Examiner* — Hoang M Nguyen
(74) *Attorney, Agent, or Firm* — Rabin & Berdo, P.C.

(57) ABSTRACT

The present invention relates to a liquid infusion device composed of a combination of a reusable module, which can be used repeatedly, and a disposable module, which is replaced after use. The present invention includes a solenoid (130) that generates magnetic force when powered, a first movable body (140) equipped with a magnet that performs a reciprocating motion driven by the magnetic force of the solenoid, and a steel plate (180) configured to interact with the magnet of the first movable body through attractive force. The reciprocating first movable body moves between a first point, where it is closest to the solenoid, and a second point, where it is farthest from the solenoid. When the solenoid is not powered, the first movable body is fixed at either the first or second point due to the attractive force between the magnet and the steel plate.

6 Claims, 10 Drawing Sheets

LIQUID INFUSION DEVICE EQUIPPED WITH A MAGNETIC RETURN-TO-ORIGIN AND FIXATION MEANS

CROSS-REFERENCE TO RELATED APPLICATION

This application claims priority to Korean Patent Application No. 10-2023-0135851, filed in the Korean Intellectual Property Office on Oct. 12, 2023, the entire contents of which are hereby incorporated by reference.

TECHNICAL FIELD

The present invention relates to a liquid infusion device capable of precisely controlling and injecting small amounts of liquid. Specifically, it pertains to a technology that ensures the magnet of the solenoid magnetic structure always returns to its origin and remains fixed when the device is in an off state, having stopped its operation. Additionally, this technology provides the necessary force for the reciprocating motion of the magnet within the solenoid magnetic structure, thereby reducing power consumption.

BACKGROUND ART

Various liquid infusion devices for injecting medical liquids such as hormones into the human body for the treatment of various diseases are widely used. For example, an insulin infusion device is used to inject liquid into a patient's body for diabetes treatment. While such infusion devices may be used by medical professionals such as doctors or nurses, in most cases, they are operated by patients themselves or by caregivers. In the case of diabetic patients, particularly pediatric diabetic patients, it is necessary to inject liquids such as insulin into the body at regular intervals. Therefore, patch-type liquid infusion devices, which can be attached to the body for a certain period, have been developed and can be used in a state where they are attached to the patient's body for a specific period. An insulin pump is a medical device used by individuals with diabetes to help control their blood sugar levels. The device delivers insulin continuously into the body to help maintain a consistent blood glucose level. It usually works by delivering insulin through a catheter placed under the skin, and it is commonly used by people with type 1 diabetes. Unlike single-use injections, an insulin pump provides a continuous supply of insulin, allowing for more precise blood sugar control. Some pumps can even connect with glucose monitors to automatically adjust insulin delivery based on blood sugar readings. This device improves convenience for users and is especially helpful for individuals who find it difficult to time their insulin injections correctly throughout the day.

It is important for such liquid infusion devices to inject the medical liquid in precise quantities. In order to inject the liquid in a measured amount, the device needs to have an internal structure that distributes the liquid accurately.

SUMMARY

The present invention aims to provide a technology in which, when the liquid infusion device has stopped operating, the magnet of the solenoid valve structure always returns to its origin and is fixed in a specific position. Additionally, it aims to provide a technology that reduces the power required for the reciprocating motion of the magnet.

The present invention relates to a liquid infusion device composed of a combination of a reusable module, which can be used repeatedly, and a disposable module, which is replaced after use.

The present invention includes a solenoid 130 that generates magnetic force when powered, a first movable body 140 equipped with a magnet that performs a reciprocating motion driven by the magnetic force of the solenoid, and a steel plate 180 configured to interact with the magnet of the first movable body through attractive force. The reciprocating first movable body moves between a first point, where it is closest to the solenoid, and a second point, where it is farthest from the solenoid. When the solenoid is not powered, the first movable body is fixed at either the first or second point due to the attractive force between the magnet and the steel plate.

The first movable body 140 can be positioned on one side of the solenoid, and the steel plate 180 can be positioned on the opposite side of the solenoid. The solenoid can be positioned on one side of the first movable body, and the steel plate can be positioned on the opposite side of the first movable body. The first movable body is composed of a central axis 142, located at the center and reciprocating due to the magnetic force of the solenoid, and an outer peripheral member 144 surrounding the central axis. The magnet may be integrated into the central axis 142.

The device further includes a piston that performs a reciprocating motion in conjunction with the reciprocation of the first movable body, discharging the liquid. When no power is supplied to the solenoid, the first movable body is fixed at either the first point or the second point, and the piston is fixed at a specific position to prevent the discharge of liquid. The reciprocating motion of the first movable body 140 consists of a first stroke, where the solenoid pushes the first movable body, and a second stroke, in which the first movable body moves in the opposite direction of the first stroke. During the first stroke, power is supplied to the solenoid, but during the second stroke, power to the solenoid is cut off, and the attractive force between the magnet of the first movable body and the steel plate pulls the first movable body, reducing power consumption.

The liquid infusion device of the present invention adopts a solenoid structure and a steel plate positioned on one side of the solenoid valve, ensuring that the magnet of the solenoid valve structure always returns to the origin and remains fixed in the original position. This prevents unintended liquid discharge from the liquid infusion device. Additionally, the invention utilizes the attractive force between the magnet of the solenoid structure and the steel plate as the energy required for the reciprocating motion of the magnet, effectively reducing power consumption. Furthermore, the steel plate shields the magnetic force emitted by the magnet in the solenoid structure, preventing its influence on the exterior of the liquid infusion device. Simultaneously, the steel plate blocks any magnetic force from external devices that may be present outside the liquid infusion device, ensuring that the external magnet's magnetic force does not affect the internal magnet and components of the liquid infusion device.

BRIEF DESCRIPTION OF THE DRAWINGS

The above and other objects, features and advantages of the present disclosure will be described with reference to the accompanying drawings described below, where similar reference numerals indicate similar elements, but not limited thereto, in which.

DETAILED DESCRIPTION

The objectives, specific advantages and novel features of the present disclosure will become more apparent from the following detailed description and the preferred embodiments, which are associated with the accompanying drawings. In addition, terms described herein are terms defined in consideration of functions in the present invention, which may vary according to the intention or convention of a user or an operator. Therefore, definitions of these terms should be made based on the contents throughout the present specification.

Hereinafter, the present disclosure will be described in detail with reference to the accompanying drawings.

Figure 1:
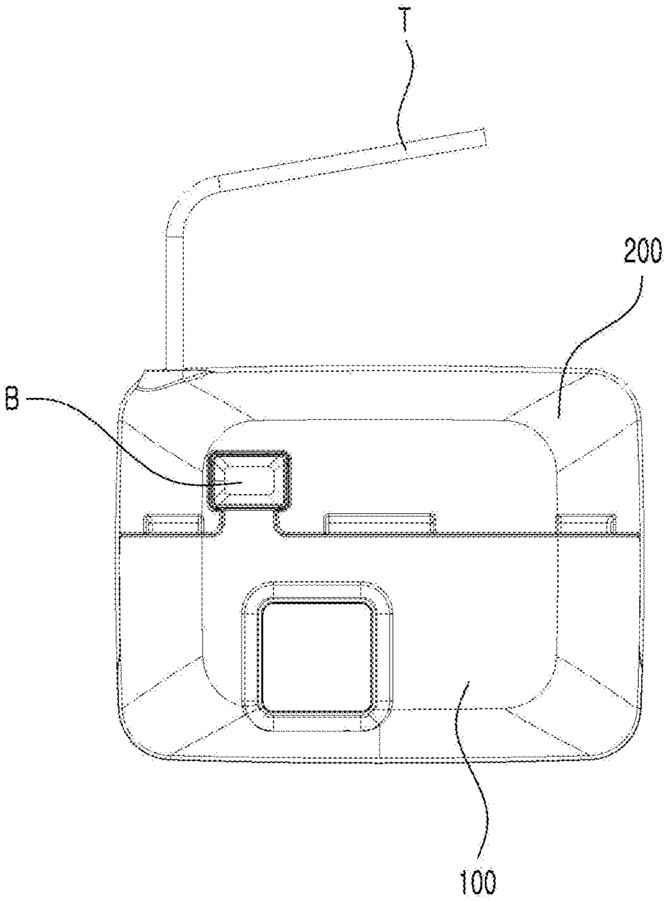
FIGS. 1 and 2 show the front and rear views of the liquid infusion device according to the present invention.
Figure 2:
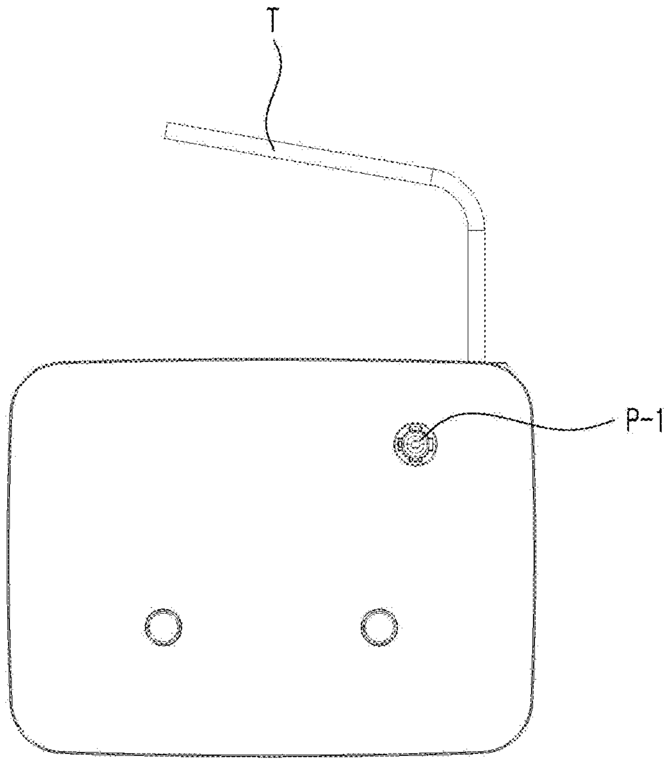
Figure 3:
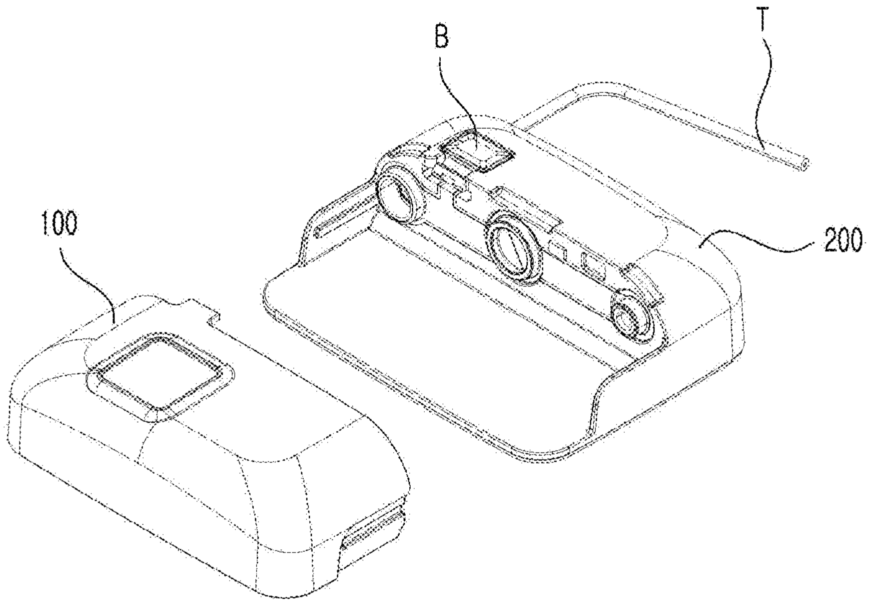
FIG. 3 shows the separated state of the reusable module and the disposable module in the liquid infusion device according to the present invention.

Referring to FIGS. 1 to 3, the liquid infusion device according to one embodiment of the present invention consists of a reusable module (a rechargeable module) 100, which can be charged and reused, and a disposable module 200, which is replaced after use. It further includes an attachment member (not shown) that attaches the disposable module to the body and a tube T that guides the liquid discharged from the disposable module to a needle (not shown) inserted into the body. Additionally, the liquid infusion device is equipped with a release button B on the front, which allows the reusable module and disposable module to be separated. By pressing this release button, the modules can be detached from each other (FIG. 3).

However, the liquid infusion device of the present invention is not limited to this type of detachable modular structure. That is, the liquid infusion device of the present invention may also have an integrated structure where the components are not separable. Therefore, the internal structure of the liquid infusion device described below can be applied to both an integrated structure and a detachable modular structure. However, the following explanation will focus on a structure composed of a reusable module 100, which can be used repeatedly, and a disposable module 200, which is replaced after use.

[Structure of the Reusable Module and Disposable Module]

Figure 4:
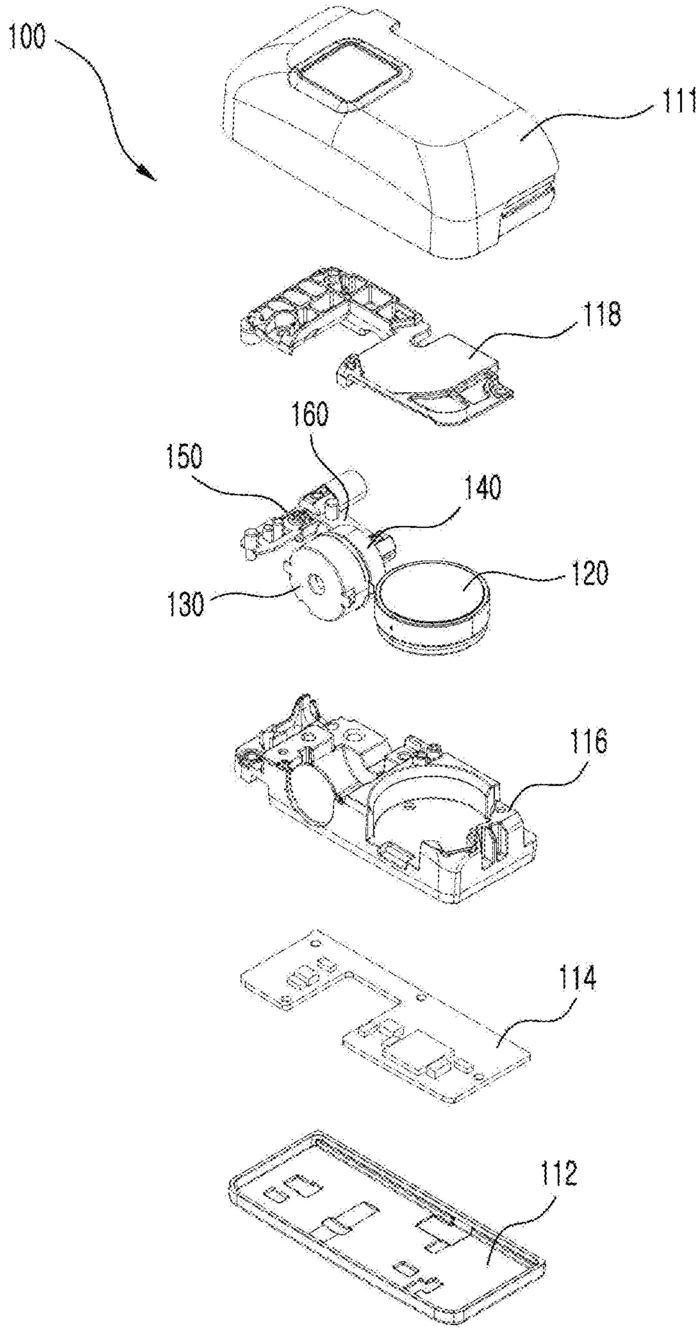
FIG. 4 is an exploded perspective view of the reusable module in the liquid infusion device according to the present invention.

Referring to FIG. 4, the reusable module 100 is designed to be separable from the disposable module 200 using the release button B and can be reused repeatedly. The reusable module 100 includes an upper case 111 and a lower case 112, and inside these cases are a main PCB 114, a lower bracket 116, and an upper bracket 118. The components housed by the upper and lower brackets include a battery 120 that stores power, a solenoid 130 that generates magnetic force powered by the battery, a first movable body 140 that reciprocates up and down by the magnetic force generated by the solenoid, and a second movable body 150 that operates in conjunction with the reciprocating motion of the first movable body to discharge the liquid stored in the disposable module 200. Additionally, a lever 160 is provided to link the up-and-down motions of the first and second movable bodies.

Figure 5:
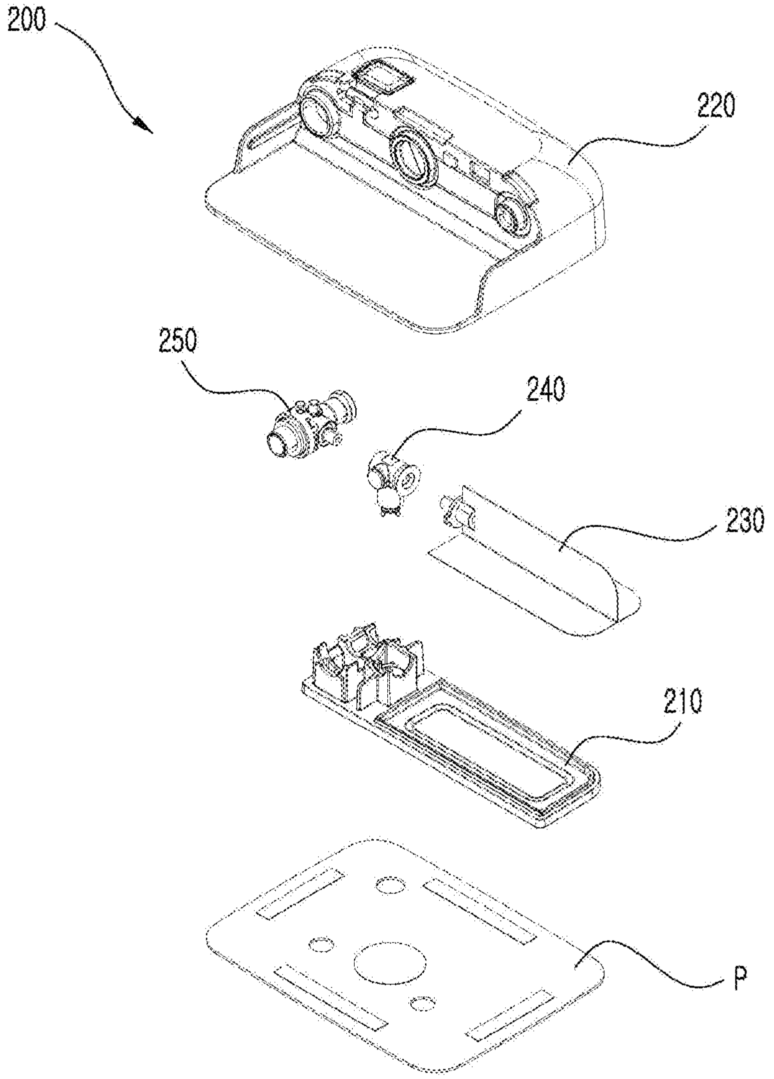
FIG. 5 is an exploded perspective view of the disposable module in the liquid infusion device according to the present invention.

FIG. 5 illustrates the disposable module 200 of the liquid infusion device according to the present invention. The disposable module 200 includes an inner case 210 and an outer case 220, which is coupled on top of the inner case. Inside these cases are components such as a reservoir 230 for storing the liquid, a piston-check valve module 250 for discharging a set amount of liquid, and a connector 240 that connects the reservoir and the piston-check valve module to deliver the liquid. The liquid stored in the reservoir 230 is transferred to the piston-check valve module 250 via the connector 240.

[Quantitative Control Structure]

The following will explain the structure for discharging the liquid, referring to FIGS. 6 to 9, in the state where the reusable module 100 and the disposable module 200 are combined. The first movable body 140 of the reusable module 100 has a moving shaft 142 inside and an outer magnet 144 around the outer circumference of the moving shaft. The moving shaft 142 moves up and down through the attraction and repulsion applied to the outer magnet 144 by the magnetic force generated by the solenoid 130. The lever 160 is arranged in an approximately horizontal direction and is a component in which both ends move up and down around a pivot axis 162 located at a specific point between the two ends.

Figure 6:
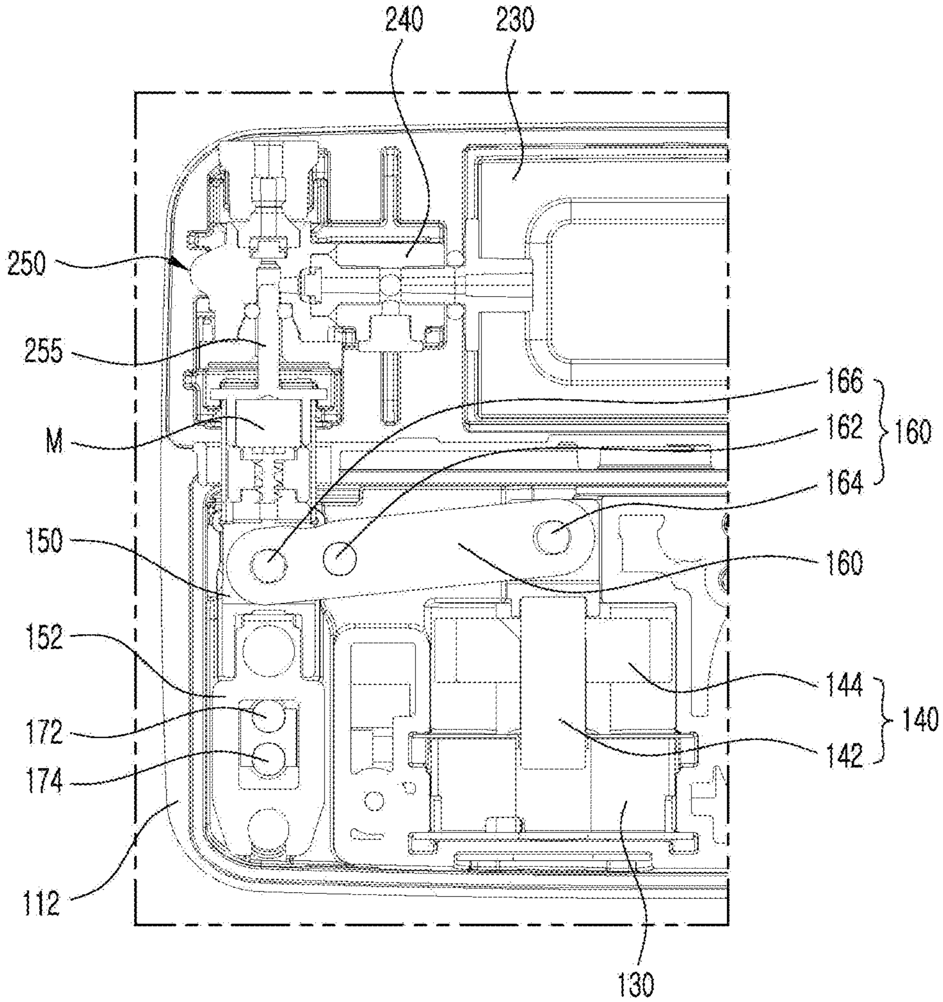
FIGS. 6 to 9 show the internal structure and operation of the piston check valve module in the liquid infusion device according to the present invention.

In the context of the up-and-down reciprocation described here, 'upward and downward direction' refers to the upward and downward movement as seen in FIG. 6, which is parallel to the longitudinal direction of the moving shaft 142. The upper end of the moving shaft 142 of the first movable body 140 is connected to one end 164 of the lever 160, and the other end 166 of the lever 160 is connected to the second movable body 150. The pivot axis 162 may be positioned closer to the other end rather than the exact center between the two ends, and in this invention, the pivot axis 162 is located closer to the second movable body.

By positioning the pivot axis closer to the second movable body, it allows for finer control of small amounts of liquid, and the second movable body can perform its reciprocating motion with relatively less force from the solenoid. In other words, the up-and-down reciprocating distance of the second movable body is smaller than that of the first movable body, allowing for more precise control of the small amount of liquid discharged from the quantitative control space 251, which will be explained below. Additionally, due to the leverage principle, the second movable body can be operated with a smaller force than the force required for the up-and-down movement of the first movable body.

Figure 8:
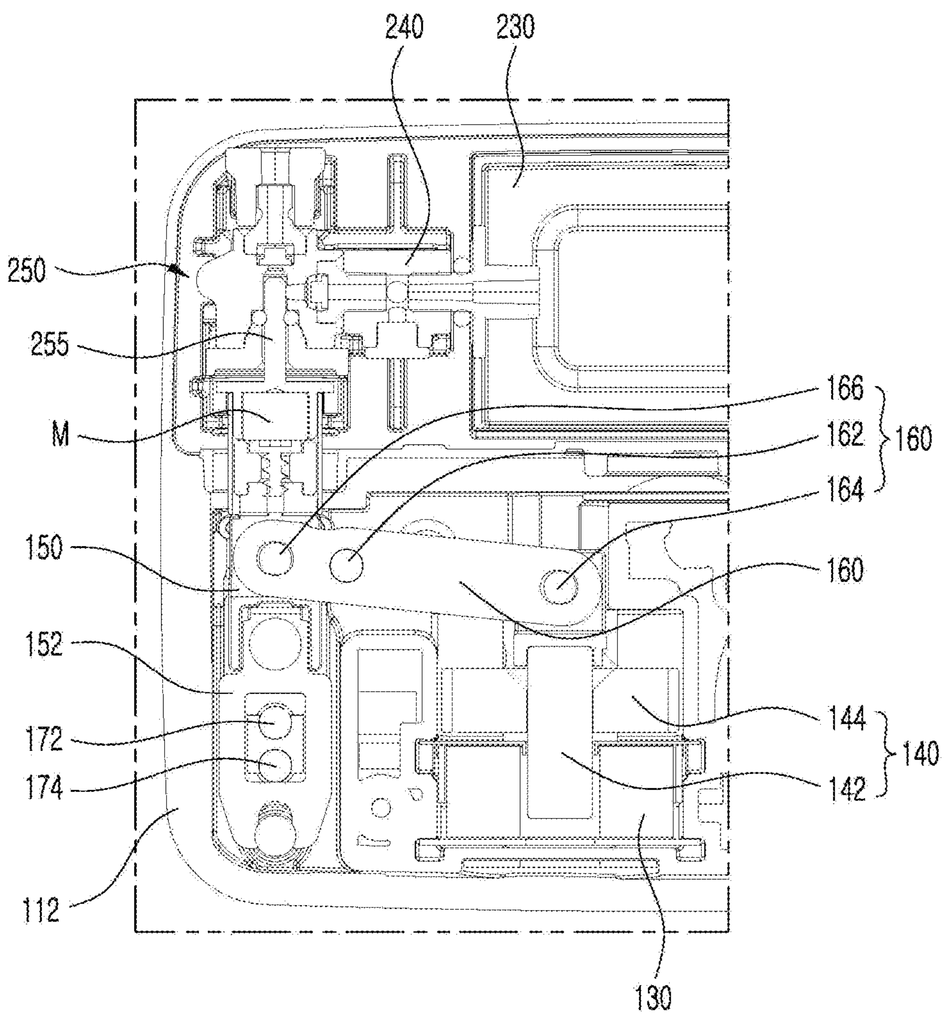

When the first movable body 140 moves forward (upward), the second movable body 150 moves backward (downward) (as shown in FIG. 6), and when the first movable body 140 moves backward (downward), the second movable body 150 moves forward (upward) (as shown in FIG. 8).

Figure 7:
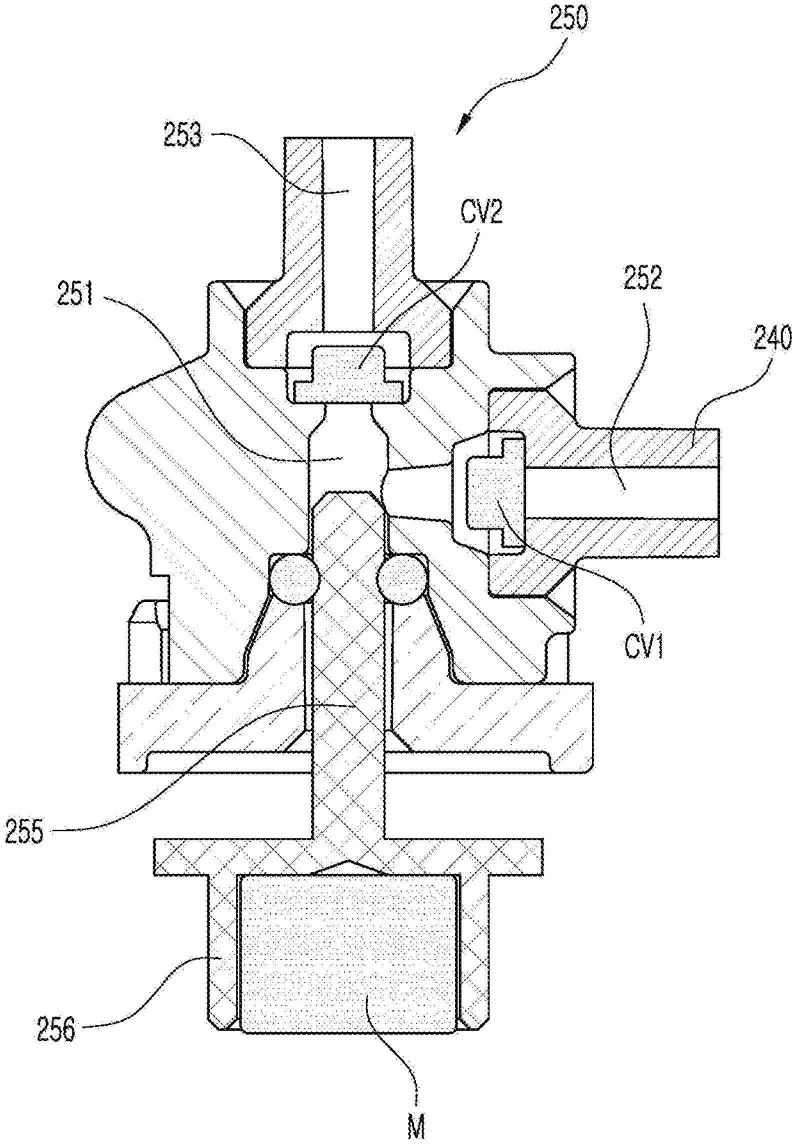
Figure 9:
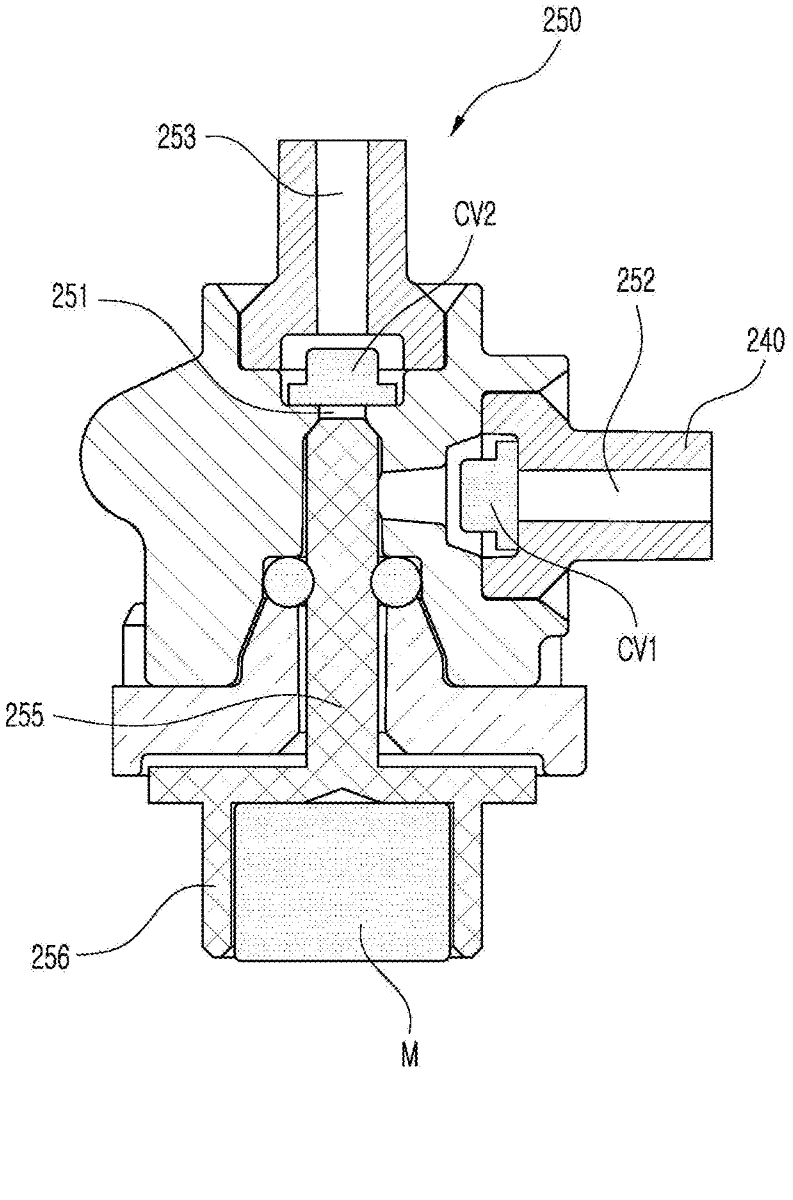

FIGS. 6 and 8 show the overall movement of the first and second movable bodies, while FIGS. 7 and 9 are enlarged detailed views that explain the operation of the piston-check valve module 250 in the disposable module 200, as shown in FIGS. 6 and 8.

The structure of the piston-check valve module 250 in the disposable module 200 is explained. The piston-check valve module 250 contains a quantitative control space 251, which is a space where a certain amount of liquid is supplied and stored. A supply passage 252 for injecting the liquid is formed laterally to the quantitative control space 251, and a discharge passage 253 for discharging the liquid is formed above the quantitative control space 251. The quantitative control space 251 is a cylindrical space formed in the vertical direction, and the piston 255 moves up and down within this space. A circular piston lower member 256, which is formed with an increased radius, is provided at the lower part of the piston 255.

The piston lower member 256 is coupled to the top of the second movable body 150 of the reusable module 100, and together with the second movable body, it performs an up-and-down reciprocating motion, causing the piston to reciprocate up and down. The piston lower member 256 is attached to the top of the second movable body 150 of the reusable module 100 through a coupling magnet M located inside it. When the first movable body 140 of the reusable module 100 moves up and down due to the operation of the solenoid 130, the second movable body 150 reciprocates accordingly, resulting in the piston 255 moving up and down within the quantitative control space 251.

When the piston 255 moves downward, the quantitative control space 251 opens, allowing the infusion process to take place as the liquid stored in the reservoir 230 is injected into the quantitative control space through the supply passage 252 (FIGS. 6 and 7). Then, when the piston 255 moves upward, the liquid in the quantitative control space 251 is discharged through the discharge passage 253 and delivered to the tube (T in FIG. 1), where it is supplied into the human body, completing the discharge process (FIGS. 8 and 9). The piston also functions as a check valve during the liquid discharge process. When the liquid is discharged from the quantitative control space, the piston 255 closes the supply passage 252 on its side outer surface, preventing the liquid from flowing back into the reservoir through the supply passage 252, thus acting as a type of check valve.

Both the supply passage 252, through which the liquid is injected into the quantitative control space 251, and the discharge passage 253, through which the liquid is discharged from the quantitative control space 251, are equipped with the first and second check valves CV1, CV2 to block reverse flow. The first check valve CV1 allows the liquid to flow only from the connector 240 into the quantitative control space 251 and prevents movement in the opposite direction, while the second check valve CV2 allows the liquid to flow only from the quantitative control space 251 toward the tube and prevents movement in the opposite direction.

The present invention, as described above, involves the construction of two check valves arranged perpendicular to each other in the supply passage and discharge passage, along with a quantitative control space utilizing a piston. These components are integrated into a single unified module, significantly reducing the product size and developing a compact structure.

By incorporating the structure of the piston-check valve module 250 in this invention, a consistent small amount of liquid is always injected into the quantitative control space 251, ensuring that it can be delivered to the human body. In other words, with a single up-and-down reciprocating motion of the piston 255, the amount of liquid corresponding to the quantitative control space is injected into the body. The specific amount of injected liquid can be determined by the size of the quantitative control space 251 (such as the diameter of the piston 255, the stroke length of the piston, etc.), and this can be adjusted based on the specific circumstances of liquid delivery.

[Piston Stroke Control]

Figure 10:
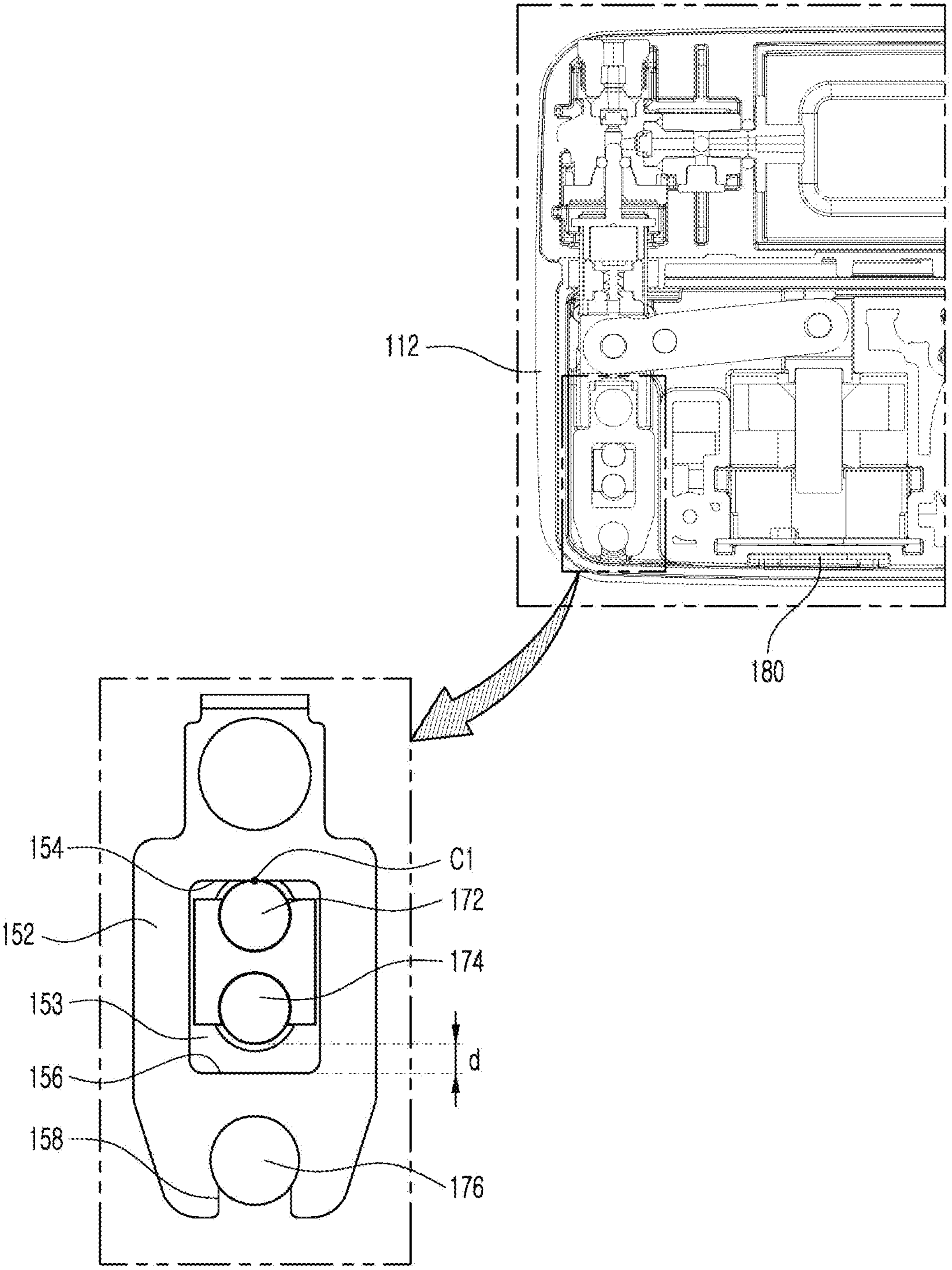
FIGS. 10 and 11 illustrate the structure that controls the vertical movement of the piston in the liquid infusion device of the present invention.
Figure 11:
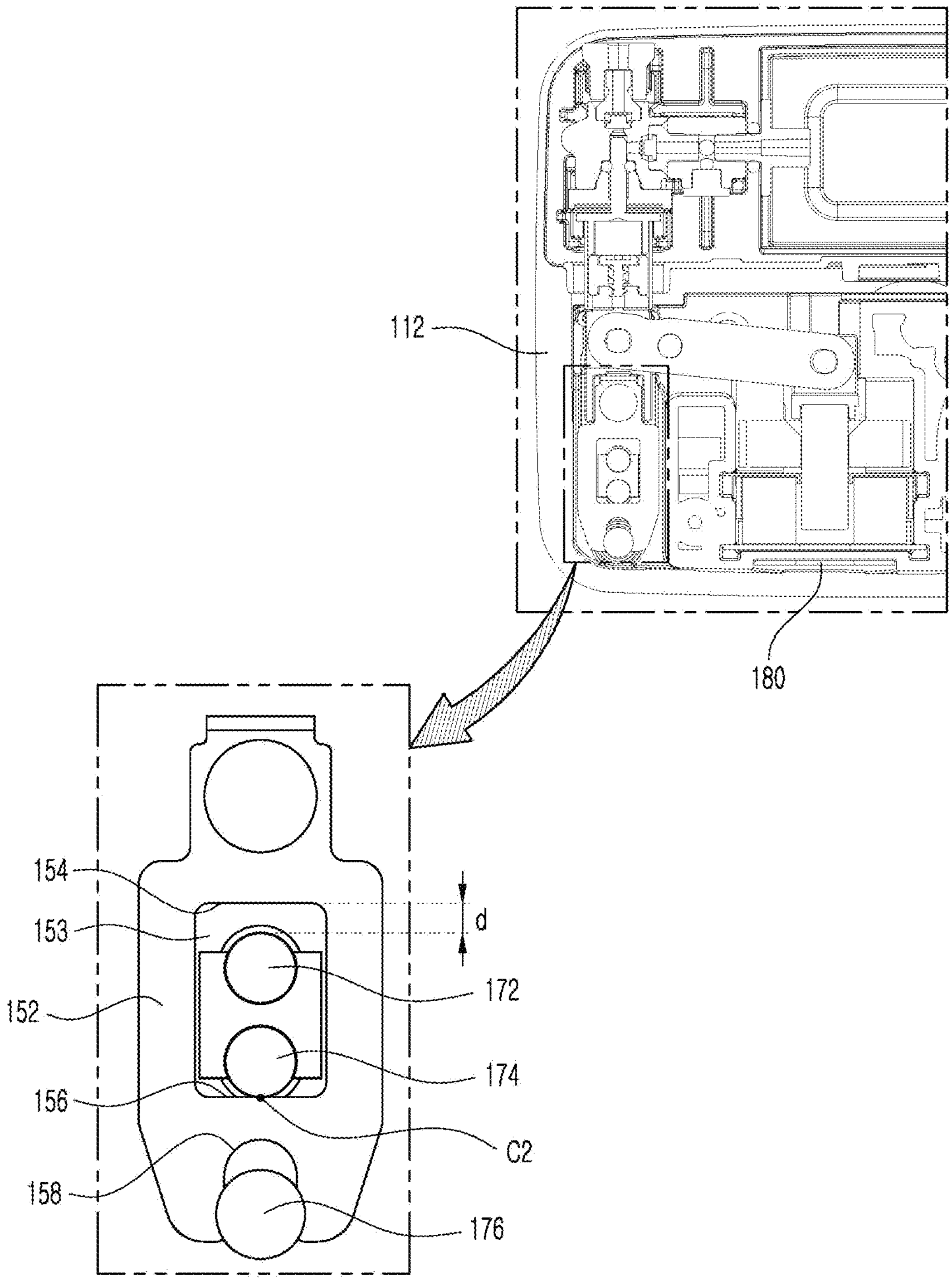

FIGS. 10 and 11 illustrate the principle of controlling the vertical reciprocating stroke (movement distance) of the second movable body 150 in the liquid infusion device of the present invention. The vertical movement distance of the second movable body determines the vertical movement distance of the piston 255 in the quantitative control space, which in turn determines the dosage of liquid delivered into the body per operation.

To control the movement of the second movable body 150, a movement limiting member 152 is provided. The movement limiting member 152 has a central opening 153, which is approximately rectangular in shape. The upper side of the inner surface of the opening is referred to as the upper surface 154, and the lower side of the inner surface is referred to as the lower surface 156.

In the lower case 112 of the reusable module 100, two protruding members are formed, spaced apart vertically. These consist of a first protruding member 172 located relatively higher and a second protruding member 174 located relatively lower. The first protruding member 172 and the second protruding member 174 protrude from the bottom surface of the lower case 112 and are positioned inside the opening 153 of the movement limiting member 152.

As explained above, the second movable body 150 moves up and down due to the operation of the solenoid 130, and the vertical movement is limited by the first protruding member 172 and the second protruding member 174, which are fixed and protrude from the lower case 112.

In FIG. 10, the second movable body has retreated downward and is positioned at the lowest point. At this time, the upper surface 154 of the opening 153 makes contact with the first protruding member 172 (contact point C1). In FIG. 11, the second movable body has advanced upward and is positioned at the highest point. At this time, the lower surface 156 of the opening 153 makes contact with the second protruding member 174 (contact point C2).

In other words, the structure of the first and second protruding members 172, 174 and the opening 153 controls the vertical movement distance of the movement limiting member (second movable body) to a defined distance (d), thereby controlling the vertical movement of the piston. In this regard, the first protruding member 172 and the second protruding member 174 act as stoppers that set the upper and lower movement limits during the reciprocating motion of the second movable body. For reference, in the present invention, the vertical movement distance (d) of the second movable body is controlled to be 0.64 mm.

The present invention, using this structure, allows the amount of liquid injected into the human body in a single injection to be extremely small and enables more precise control over the amount of liquid.

[Return to Origin and Fixation of the First Movable Body]

The present invention provides a structure in which, when the liquid infusion device is not powered, meaning the device is in an off state, the first movable body 140 always returns to a specific origin point and remains fixed at that point without moving (this is referred to as the 'origin fixation state'). In this invention, the return mechanism for the origin fixation state of the first movable body is a steel plate 180, located inside the lower bracket 116 of the reusable module 100 case. The steel plate of the present invention is shown as part 180 in FIGS. 4, 6, and 8, and it may be a circular plate with a uniform thickness.

As described above, the first movable body 140 consists of a central axis 142 and an outer peripheral member 144, and the entire first movable body 140 may be composed of a magnet to enable reciprocating motion through the magnetic force of the solenoid. Alternatively, only the central axis 142 may be composed of a magnet.

The first movable body 140 of the present invention performs a reciprocating motion driven by the magnetic force of the solenoid, moving between a first point (as shown in FIG. 8) where it is closest to the solenoid and a second point (as shown in FIG. 6) where it is farthest from the solenoid. However, if the liquid infusion device turns off and power is no longer supplied to the solenoid while the first movable body is in motion, the first movable body stops at its current position.

In this invention, due to the attractive force between the magnet of the first movable body 140 and the steel plate 180, the first movable body moves to the first point, where it is fixed in place by magnetic force. Regardless of where the first movable body 140 is positioned during its reciprocating motion, when the operation of the liquid infusion device stops, the first movable body returns to the origin (the first point). In other words, whether the first movable body 140 is positioned at the second point during its reciprocating motion or somewhere between the first and second points, when the device is turned off, the first movable body returns to the origin and remains fixed in what is referred to as the origin fixation state.

When the first movable body is fixed at the origin, unintended liquid discharge from the liquid infusion device can be prevented. Without a fixation mechanism for the first movable body 140, such as the one in the present invention, if the liquid infusion device is shaken violently or subjected to an impact, the first movable body could move even when the power is off. This movement of the first movable body could be transmitted to the piston, potentially causing unintended liquid discharge. The present invention prevents such unintended liquid discharge by securely fixing the position of the first movable body at a specific point when the power is off.

In the embodiment and drawings of the present invention, the steel plate 180 is shown positioned on the opposite side of the first movable body relative to the solenoid 130. However, for the purpose of origin fixation, it is also possible to place the steel plate in a different position. Specifically, it would be possible to position the steel plate on the opposite side of the solenoid relative to the first movable body (above the first movable body as shown in FIG. 6). In this case, when the device's power is turned off, the first movable body would return to the second point (as shown in FIG. 6) and be fixed in that position.

Additionally, the present invention effectively reduces the power consumption by utilizing the attractive force between the magnet of the solenoid structure and the steel plate as the energy required for the reciprocating motion of the first movable body. In other words, the solenoid pushes and pulls the first movable body during the reciprocating motion. The process in which the solenoid pushes the first movable body is called the first stroke, and the process in which the first movable body moves in the opposite direction of the first stroke is called the second stroke. In the first stroke, power is supplied to the solenoid to push the first movable body, while in the second stroke, power to the solenoid is cut off, and the attractive force between the magnet of the first movable body and the steel plate pulls the first movable body. This allows power to be supplied during only one of the two movements, thereby reducing the power consumption. The selective power supply and cut-off is performed by the control unit provided on the main PCB of the present invention.

Additionally, the present invention prevents the magnetic force emitted by the magnet of the solenoid structure from affecting the exterior of the liquid infusion device by using the steel plate as a shield. Simultaneously, the steel plate blocks the magnetic force from any external magnets that may be present outside the liquid infusion device, thereby preventing the magnetic force of external magnets from influencing the internal magnets and components of the liquid infusion device.

Although the present disclosure has been described in connection with some examples herein, the present disclosure should not be limited to those examples only, and various other changes and modifications made by those skilled in the art from the basic concept of the disclosure are also within the scope of the claims appended herein.

What is claimed is:

1. A liquid infusion device comprising:

a solenoid (130) that generates magnetic force when powered;

a first movable body (140) equipped with a magnet that performs a reciprocating motion driven by the magnetic force of the solenoid;

a second movable body (150), which is spaced a predetermined distance from the first movable body and arranged in parallel, performing a reciprocating motion in conjunction with the reciprocating motion of the first movable body;

a lever (160), having one end coupled to the top of the first movable body and the other end coupled to the second movable body, with a pivot axis positioned at a specific point between both ends, a steel plate (180) configured to interact with the magnet of the first movable body through magnetic attractive force;

a reservoir (230) that stores liquid; and a piston-check valve module (250) that receives the liquid from the reservoir and discharges the liquid out of the piston-check valve module, the piston-check valve module including a piston that is connected to the second movable body, the piston performing a reciprocating motion in conjunction with the reciprocating motion of the second movable body;

wherein the reciprocating first movable body moves between a first point, where it is closest to the solenoid, and a second point, where it is farthest from the solenoid, and when no power is supplied to the solenoid, the magnetic attractive force between the magnet and the steel plate causes the first movable body to move to either the first or second point and remain fixed there.

2. The liquid infusion device according to claim 1, wherein the first movable body (140) is positioned on one side of the solenoid, and the steel plate (180) is positioned on the opposite side of the solenoid.

3. The liquid infusion device according to claim 1, wherein the solenoid is positioned on one side of the first movable body, and the steel plate is positioned on the opposite side of the first movable body.

4. The liquid infusion device according to claim 1, wherein the first movable body consists of a central axis (142), positioned at the center and performing a reciprocating motion driven by the magnetic force of the solenoid, and an outer peripheral member (144) surrounding the central axis, and the central axis (142) is the magnet.

5. The liquid infusion device according to claim 1, when no power is supplied to the solenoid, the first movable body is fixed at either the first or second point, and the piston is fixed at a specific position, thereby preventing the discharge of liquid.

6. The liquid infusion device according to claim 1, wherein the reciprocating motion of the first movable body (140) consists of a first stroke, in which the solenoid pushes the first movable body, and a second stroke, in which the first movable body moves in the opposite direction of the first stroke and in the first stroke, power is supplied to the solenoid, while in the second stroke, the power supply to the solenoid is cut off, and the first movable body is pulled by the magnetic attractive force between the magnet of the first movable body and the steel plate, thereby reducing power consumption.

* * * * *